United States Patent [19]

Pasternak

[11] Patent Number: 5,160,046
[45] Date of Patent: Nov. 3, 1992

[54] MEMBRANE SEPARATION PROCESS

[75] Inventor: Mordechai Pasternak, Spring Valley, N.Y.

[73] Assignee: Texaco Inc., White Plains, N.Y.

[21] Appl. No.: 793,900

[22] Filed: Nov. 18, 1991

[51] Int. Cl.⁵ .............................................. B01D 61/36
[52] U.S. Cl. ........................................ 210/640; 55/16
[58] Field of Search .............. 210/500.39, 640; 55/16, 55/158; 159/DIG. 27; 203/DIG. 17, 99, 91

[56] References Cited

U.S. PATENT DOCUMENTS 4,865,745  9/1989  Pasternak ...................... 210/500.39

Primary Examiner—Frank Sever
Attorney, Agent, or Firm—Robert A. Kulason; James J. O'Loughlin; Carl G. Seutter

[57] ABSTRACT

Aqueous solutions of organic oxygenates, typified by concentrated aqueous solutions of ethanol or isopropanol, are dewatered by pervaporation through a polyimine membrane which has been interfacially cross-linked with a polyisocyanate or a poly(carbonyl chloride).

25 Claims, No Drawings

MEMBRANE SEPARATION PROCESS

FIELD OF THE INVENTION

This invention relates to a method of treating aqueous solutions. More particularly it relates to a membrane process for treating concentrated aqueous solutions to yield product characterized by decreased content of water.

BACKGROUND OF THE INVENTION

As is well known to those skilled in the art, it is possible to remove water from mixtures thereof with organic liquids by various techniques including adsorption or distillation. These conventional processes, particularly distillation, are however, characterized by high capital cost. In the case of distillation for example, the process requires expensive distillation towers, heaters, heat exchangers (reboilers, condensers, etc.), together with a substantial amount of auxiliary equipment typified by pumps, collection vessels, vacuum generating equipment, etc.

Such operations are characterized by high operating costs-principally costs of heating and cooling—plus pumping, etc.

Furthermore the properties of the materials being separated, as is evidenced by the distillation curves, may be such that a large number of plates may be required, etc. When the material forms an azeotrope with water, additional problems may be present which for example, could require that separation be effected in a series of steps (e.g. as in two towers) or by addition of extraneous materials to the system.

There are also comparable problems which are unique to adsorption systems.

It has been found to be possible to utilize membrane systems to separate mixtures of miscible liquids by reverse osmosis. In this process, the charge liquid is brought into contact with a membrane film; and one component of the charge liquid preferentially permeates the membrane. The permeate is then recovered as a liquid from the downstream side of the film.

Composite membranes prepared by interfacial cross-linking have been used in various processes including water purification, reverse osmosis, organic/organic separations, gas/liquid separation, etc. In such processes, the charge/retentate side of the membrane is commonly at a high pressure (typically 700 psig) and the permeate side of the membrane is commonly at atmospheric pressure The permeate is recovered in liquid phase.

Illustrative of such processes are those set fort in the following patents:

U.S. Pat. No. 5,037,555 to Texaco Inc as assignee of Mordechai Pasternak and Abraham Morduchowitz is directed to desalination of water by reverse osmosis across a membrane of a polyimine polymer which has been cross-linked with an isocyanate or a carbonyl chloride cross-linking agent.

U.S. Pat. No. 4,865,745 to Texaco Inc as assignee of Mordechai Pasternak is directed to dewatering of dilute aqueous solutions of organic oxygenates by a pressure drive process across a membrane of a polyimine polymer which has been cross-linked with an isocyanate or a carbonyl chloride cross-linking agent.

U.S. Pat. No. 4,897,091 to Texaco Inc as assignee of Mordechai Pasternak and Richard Beaupre is directed to separation of carbon dioxide from solution thereof in methanol by use in a pressure driven process, of a membrane which is the reaction product of (i) a polyamine and (ii) a polyisocyanate or a poly (carbonyl chloride).

U.S. Pat. No. 4,985,138 to Texaco Inc as assignee of Mordechai Pasternak is directed to separation of dewaxed oil from dewaxing solvent by a pressure driven process across a polyurea membrane.

There is also a body of prior art directed to separation of water from dilute solutions of various compositions by pervaporation wherein the permeate is recovered in vapor phase under vacuum. Illustrative of such processes are those set forth in the following patents:

U.S. Pat. No. 4,802,988 to Texaco Inc as assignee of John Reale, Jr. and Craig R. Bartels is directed to separation of water from ethylene glycol by pervaporation across a membrane of polyvinyl alcohol which has been cross-linked with an aliphatic polyaldehyde containing at least three carbon atoms.

U.S. Pat. No. 5,004,861 to Texaco Inc as assignee of Mordechai Pasternak, Craig R. Bartels, and John Reale, Jr. is directed to separation of water from a charge mixture of hydrocarbon and organic oxygenate by use, in a pervaporation process, of (i) a membrane of polyvinyl alcohol which has been cross-linked with a polyaldehyde containing at least three carbon atoms or (ii) a composite membrane of blended polyvinyl alcohol and polyacrylic acid.

U.S. Pat. No. 4,935,144 to Texaco Inc as assignee of Mordechai Pasternak, Craig R. Bartels, and John Reale, Jr. is directed to separation of aqueous solutions of organic oxygenates by pervaporation across a membrane of polyvinyl alcohol which has been cross-linked with a polyaldehyde containing at least three carbon atoms.

U.S. Pat. No. 4,910,344 to Texaco Inc as assignee of Mordechai Pasternak, Craig R. Bartels, and John Reale, Jr. is directed to separation of water from a charge mixture of hydrocarbon and organic oxygenates by pervaporation across a composite membrane of polyvinyl alcohol and a polyarcylic acid.

U.S. Pat. No. 4,992,176 to Texaco Inc as assignee of Craig R. Bartels is directed to dehydration of organic oxygenates by pervaporation through a membrane of dibromo butane-cross-linked polyvinyl pyridine.

U.S. Pat. No. 5,032,278 to Texaco Inc as assignee of John Reale, Jr. is directed to dehydration of hydrocarbon/organic oxygenate mixtures by pervaporation across a heat-treated polyethylene imine membrane.

Additional background may be obtained from (i) U.S. Pat. No. 4,411,787 to UOP as assignee of Riley; (ii) J. E. Cadotte et al, J. Macromol. Sci-Chem A15 (5) p 727 (1981); (iii) L. T. Rozelle et al Chapter 12 in *Reverse Osmosis and Synthetic Membranes* S. Sourirajan (Ed). See also the references cited in the above patents.

It is an object of this invention to provide a process for dewatering aqueous solutions. Other objects will be apparent to those skilled in the art.

STATEMENT OF THE INVENTION

In accordance with certain of its aspects, this invention is directed to a method which comprises passing a charge aqueous solution of an organic oxygen-containing liquid component which is soluble in water into contact with, as pervaporation membrane, a non-porous separating polyimine polymer layer which has been interfacially crosslinked with a polyisocyanate —NCO or with a poly(carbonyl chloride) —COCl crosslinking agent;

maintaining a pressure drop across said membrane thereby forming a high pressure retentate containing increased content of organic oxygen-containing component and decreased content of water and a low pressure permeate of increased content of water and decreased content of organic oxygen-containing component;

maintaining the pressure on the low pressure discharge side of said membrane below the vapor pressure of said permeate thereby maintaining said permeate in vapor phase;

maintaining the pressure on the high pressure retentate side of said membrane above the vapor pressure of said charge aqueous solution and of said retentate thereby maintaining said charge aqueous solution and said retentate in liquid phase;

recovering said permeate of increased content of water and decreased content of organic oxygen-containing component, in vapor phase from the low pressure discharge side of said membrane; and recovering said retentate of increased content of organic oxygen-containing component and decreased content of water, in liquid phase from the high pressure side of said membrane.

DESCRIPTION OF THE INVENTION

The Charge Solution

The charge aqueous solution of organic oxygen-containing liquid component which may be treated by the process of this invention may include oxygen-containing compounds such as alcohols, glycols, organic carboxylic acids, polyols, aldehydes, ketones, etc. When the oxygen-containing component is an alcohol, it maybe for example ethanol, propanol, isopropanol, n-butanol, isobutanol, t-butanol, hexanols, octanols, etc. When the oxygen-containing component is a glycol it may be for example ethylene glycol, propylene glycol, butylene glycol, etc. When the oxygen-containing component is a polyol, it maybe for example glycerine, sorbitol, pentaerythritol, trimethylolmethane, polyoxyethylene (or polyoxypropylene) polyol, etc. When the oxygen-containing component is an acid, it may for example be acetic acid, propionic acid, butyric acid, etc. When the oxygen-containing component is an aldehyde, it may for example be formaldehyde, acetaldehyde, etc. When the oxygen-containing component is a ketone, it may for example be acetone, methyl ethyl ketone, acetophenone, etc.

It is a particular feature of the process of this invention that the advantages thereof may be most readily apparent when the charge aqueous solution is a concentrated aqueous solution.

It is also possible to utilize the process of this invention with immiscible mixtures or with partially miscible mixtures.

Although the advantages may be attained when the charge concentrated solution contains less than say 70 w % or more of organic oxygen-containing component, it may be found that desired results are be obtained when the charge solutions are at or above the 90 w % level. It is particularly found that desired results may be attained when the charge contains 95 w %-98+w % oxygenate.

The instant process may find particular use in connection with other concentration techniques. For example, a particular charge solution may be concentrated by distillation up to a point at which further concentration by distillation maybe uneconomical. A charge may, for example, be concentrated to a point at which an azeotrope is formed. In alternative aspects, the process of the instant invention may be employed first, followed, for example, by distillation. Clearly in each case the number of separation steps and the particular sequence will depend on the economics of the particular system which of course depend on the composition and properties of the charge solution.

The process of this invention is found to be particularly useful in treating charge solutions containing ethyl alcohol (in azeotropic concentration of 95 w %) or isopropanol (in concentration of say 85 w %) to recover product containing decreased quantities of water.

Illustrative charge solutions which may be employed in practice of the process of this invention may include:
(i) 95 w % ethyl alcohol, 5 w % water.
(ii) 80 w % ethylene glycol, 20 w % water.
(iii) 95 w % ethylene glycol, 1 w % water.
(iv) 95 w % acetone, 5 w % water.
(v) 92 w % acetic acid, 8 w % water.
(vi) 75 w % acetaldehyde, 25 w % water.
(vii) 85 w % isopropanol, 15 w % water

The Membrane Assembly

Practice of the process of this invention may be carried out by use of a composite structure which in one preferred embodiment may include (i) a carrier layer which provides mechanical strength, (ii) a porous support layer, and (iii) a separating layer across which separation occurs.

The composite structure of this invention includes a multi-layer assembly which in the preferred embodiment, preferably includes a porous carrier layer which provides mechanical strength and support to the assembly.

The Carrier Layer

This carrier layer, when used, is characterized by its high degree of porosity and mechanical strength. It may be fibrous or non-fibrous, woven or non-woven. In the preferred embodiment, the carrier layer may be a porous, flexible, non-woven fibrous polyester.

A preferred non-woven polyester carrier layer may be formulated of non-woven, thermally-bonded strands of polyester and characterized by a fabric weight of 80±8 grams per square yard, a thickness of 4.2±0.5 mils, a tensile strength (in the machine direction) of 31 psi and (in cross direction) of 10 psi, and a Frazier air permeability of 6 cu.ft/min.sq. ft. @0.5 inches of water.

The Porous Support Layer

The porous support layer useful in practice of the process of this invention may be preferably formed of an ultrafiltration membrane—preferably formed of polyacrylonitrile polymer. Typically the polyacrylonitrile may be of thickness of 40–80 microns, say 50 microns and is preferably characterized by a pore diameter of less than about 500 A and typically about 200 A. This corresponds to a molecular weight cut-off less than about 50,000, typically about 40,000. A preferred commercially available porous support layer is the Daicel DUY-L brand of polyacrylonitrile (molecular weight cut-off of about 40,000) which is available on a non-woven, thermally bonded polyester carrier layer of polyester.

In another embodiment, the porous support layer may be formed of a sheet of polysulfone polymer. Typically the polysulfone may be of thickness of 40-80 microns, say 50 microns and of molecular weight $\overline{M}_n$ of 5,000-100,000, preferably 20,000-60,000 say 40,000. The polysulfone is preferably characterized by a pore size of about 100 Å. This corresponds to a molecular weight cut-off of about 20,000.

The sulfone polymers which may be employed may include those made from cumene containing isopropylidene groups in the backbone; e.g.

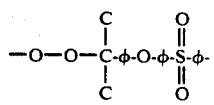

These isopropylidene sulfones, containing as repeating units ether-aromatic-isopropylidene-aromatic-ether aromatic-sulfone-aromatic groups, may typically have a molecular weight $\overline{M}_n$ of 15,000-30,000, water absorption (at 20° C.) of about 0.85 w %, a glass transition temperature of 449° K., a density of 1.25 mg/m$^3$, a tensile strength (at 20° C.) at yield of 10,000 psi, and a coefficient of linear thermal expansion of $1.6 \times 10^{-5}$ mm/mm/° C.

The Separating Layer

The separating layer which permits attainment of separation in accordance with the process of this invention includes a non-porous film or membrane of 0.2-1 microns, say about 0.5 microns of a polyimine polymer of molecular weight $\overline{M}_n$ of 40,000-100,000, say about 60,000 which is cross-linked by urea or amide linkages.

The separating layer may preferably be prepared by cross-linking a polyimine polymer.

In the preferred embodiment, a polyimine polymer is cross-linked. Polyimine polymers are characterized by the presence of recurring -N-R''- groups as integral parts of the main polymer chain. Typical structural formulae of linear polyimines maybe represented as $$H_2N-R''[NH-R'']_n-NH_2$$

wherein n represents the degree of polymerization or number of recurring groups in the polymer chain.

Illustrative polyimine polymers include those of molecular weight $\overline{M}_n$ of 40,000-100,000, say 60,000.

Suitable polyimines may include, the first listed being preferred:

TABLE

A. Cordova Chemical Company Corcat P-600 (now Hoechst-Celanese P-600 XE) brand of polyethylenimine resin membrane $\overline{M}_n$ of 60,000) in 33 w % aqueous solution—Brookfield viscosity @25° C. of 5000 Cp, Sp, Gr @25° C. of 1.04-1.06, and pH of 10-11, having the formula

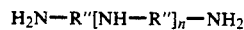

wherein R is H or

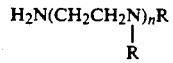

(containing 30% primary, 40% secondary, and 30% tertiary amines)

B. Dow Chemical Co Tydex 12 brand of polyethyleneimine membrane ($\overline{M}_n$ of 50,000) in 30 w % aqueous solution having the same formula as the Corcat P-600 membrane.

Cross-linking of the preformed polyimine polymer may be effected by contact with, cross-linking agent,

wherein a is 0 or 1

When the isocyanate cross-linking agent R''(NCO)$_b$ is employed, the cross-linking forms urea bonds. When the carbonyl chloride cross-linking agent R''(COCl)$_b$ is employed, the cross-linking forms amide bonds.

In the above formula:
R'' is a polyvalent hydrocarbon moiety;
a is 0 or 1; and
b is an integer greater than 1.
R'' may be a polyvalent hydrocarbon moiety such as in 1,3,5-benzene tri(carbonyl) chloride). In the preferred embodiment, R'' may be a divalent moiety.

In the above formula, R'' may preferably be a hydrocarbon group selected from the group consisting of alkylene, aralkylene, cycloalkylene, arylene, and alkarylene, including such radicals when inertly substituted. When R'' is alkylene, it may typically be methylene, ethylene, n-propylene, iso-propylene, n-butylene, i-butylene, sec-butylene, amylene, octylene, decylene, octadecylene, etc. When R'' is aralkylene, it may typically be benzylene, beta-phenylethylene, etc. When R'' is cycloalkylene, it may typically be cyclohexylene, cycloheptylene, cyclooctylene, 2-methylcycloheptylene, 3-butylcyclohexylene, 3-methylcyclohexylene, etc. When R'' is arylene, it may typically be phenylene, naphthalene, etc. When R'' is alkarylene, it may typically be tolylene, xylylene, etc. R'' may be inertly substituted i.e. it may bear a non-reactive substituent such as alkyl, aryl, cycloalkyl, ether, etc. Typically inertly substituted R'' groups may include 3-methoxypropylene, 2-ethoxyethylene, carboethoxymethylene, 4-methylcyclohexylene, p-methylphenylene, p-methylbenzylene, 3-ethyl- 5-methylphenylene, etc. The preferred R'' groups may be phenylene or lower alkylene, i.e. C$_1$-C$_{10}$ alkylene, groups including e.g. methylene, ethylene, n-propylene, i-propylene, butylene, amylene, hexylene, octylene, decylene, etc. R'' may preferably be phenylene or hexamethylene.

wherein a is 0 or 1 and b is an integer greater than 1, may be a polyisocyanate when a is 1. When a is 0, the second reactant may be a poly(carbonyl chloride). Preferably a is 1 and b is 2 i.e. the preferred second reactant is a diisocyanate when the first reactant is polyethyleneimine.

The preferred polyisocyanates (i.e. monomeric compounds bearing a plurality of —NCO isocyanate groups) may include those which contain an aromatic nucleus, typically a toluene diisocyanate or a phenylene diisocyanate.

The preferred poly(carbonyl chlorides) i.e. monomeric compounds bearing a plurality of —COCl carbonyl chloride groups) may include those which contain an aromatic nucleus.

Illustrative cross-linking agent may include the following, the first listed being preferred:

TABLE 2,4-toluene diisocyanate
meta-phenylene diisocyanate
3,5-toluene diisocyanate
para-phenylene diisocyanate
hexamethylene diisocyanate
isophthaloyl dichloride
terephthaloyl dichloride
1,3,5 benzene tri(carbonyl chloride)
suberoyl dichloride In practice of the process of this invention, the separating membrane layer may be cross-linked by an interfacial reaction. This may be effected as by casting the membrane on a support layer, such as the preferred porous polyacrylonitrile support. In this aspect of the invention, the polyimine membrane (preferably in 1 w % aqueous solution) is poured onto a support membrane and allowed to migrate into the pores of the support membrane over 1-8 minutes, say 2 minutes at 20°-30° C., say 25° C. The membrane is then held in vertical position for 1 minute to drain excess solution.

The cross-linking agent (e.g. 2,4-toluene diisocyanate), preferably in a 1w % solution in a hydrocarbon such as hexane, is then poured in equivalent amount carefully onto the surface of the separation membrane. The cross-linking agent is allowed to interfacially cross-link the polymer at 20° C.-30° C., say 25° C. for 10-60 seconds, say 30 seconds. The excess of unreacted cross-linking agent may then carefully be poured off to terminate the interfacial reaction process. The so-formed assembly may be heat cured at 120°-140° C., say 125° C. for 10-30 minutes, say 15 minutes. During this curing, thermal cross-linking may complete the fabrication of the barrier layer.

The Composite Membrane

It is a feature of this invention that it may utilize a composite membrane which comprises (i) an optional carrier layer characterized by porosity and mechanical strength, for supporting a porous support layer, (ii) preferably a porous support layer such as a polyacrylonitrile membrane, of thickness of 40-80 microns, and of molecular weight cut-off of less than about 50,000, and (iii) as a non-porous separating layer a polyimine of molecular weight of $\overline{M}_n$ of 40,000-100,000, which has been interfacially cross-linked with a polyisocyanate or a poly(carbonyl chloride).

It is possible to utilize a spiral wound module which includes a non-porous separating layer membrane mounted on a porous support layer and a carrier layer, the assembly being typically folded and bonded or sealed along all the edges but an open edge—to form a bag-like unit which preferably has the separating layer on the outside. A cloth spacer, serving as the permeate or discharge channel is placed within the bag-like unit. The discharge channel projects from the open end of the unit.

There then placed on one face of the bag-like unit, adjacent to the separating layer, and coterminous therewith, a feed channel sheet—typically formed of a plastic net.

The so-formed assembly is wrapped around a preferably cylindrical conduit which bears a plurality of perforations in the wall—preferably in a linear array which is as long as the width of the bag-like unit. The projecting portion of the discharge channel of the bag-like unit is placed over the perforations of the conduit; and the bag-like unit is wrapped around the conduit to form a spiral wound configuration. It will be apparent that, although only one feed channel is present, the single feed channel in the wound assembly will be adjacent to two faces of the membrane layer. The spiral wound configuration may be formed by wrapping the assembly around the conduit a plurality of times to form a readily handleable unit. The unit is fitted within a shell (in manner comparable to a shell-and-tube heat exchanger) provided with an inlet at one end and an outlet at the other. A baffle like seal between the inner surface of the shell and the outer surface of the spiral-wound unit prevents fluid from bypassing the operative membrane system and insures that fluid enters the system principally at one end. The permeate passes from the feed channel, into contact with the separating layer and thence therethrough, into the permeate channel and thence therealong to and through the perforations in the conduit through which it is withdrawn as net permeate.

In use of the spiral wound membrane, charge liquid is permitted to pass through the plastic net which serves as a feed channel and thence into contact with the non-porous separating membranes. The liquid which does not pass through the membranes is withdrawn as retentate. The vapor which permeates the membrane passes into the volume occupied by the permeate spacer and through this permeate channel to the perforations in the cylindrical conduit through which it is withdrawn from the system.

In another embodiment, it is possible to utilize the system of this invention as a tubular or hollow fibre. In this embodiment, the polyacrylonitrile porous support layer may be extruded as a fine tube with a wall thickness of typically 0.001-0.1 mm. The extruded tubes are passed through a bath of polyethyleneimine polymer which is thereafter cross-linked and cured in situ. A bundle of these tubes is secured (with an epoxy adhesive) at each end in a header; and the fibres are cut so that they are flush with the ends of the header. This tube bundle is mounted within a shell in a typical shell-and-tube assembly.

In operation, the charge liquid is admitted to the tube side and passes through the inside of the tubes and exits as retentate. During passage through the tubes, permeate passes through the non-porous separating layer and permeate is collected in the shell side.

Pervaporation

It is a feature of the non-porous cross-linked polyimine separating layer that it is found to be particularly effective when used in a pervaporation process. In pervaporation, a charge liquid containing a more permeable and a less permeable component is maintained in contact with a non-porous separating layer; and a pressure drop is maintained across that layer. The permeate side is maintained at a pressure below the vapor pressure of the permeate—typically at about 1 mm.Hg. A portion of the charge liquid dissolves into the membrane and diffuses therethrough. The permeate passes through the membrane and exits as a vapor.

It is a feature of this invention that the membrane may be particularly useful in processes for treatment of aqueous solutions.

In practice of the process of this invention, the charge aqueous in liquid phase typically at 40° C.–80° C., say 70° C. may be passed into contact with the non-porous separating layer of the interfacially cross-linked membrane. A pressure drop is maintained across the membrane. The feed or charge side of the membrane is typically at atmospheric pressure; and the permeate or discharge side of the membrane is at pressure below the vapor pressure of the permeate—typically 1–50 mmHg, say about 1 mm.Hg.

The permeate which passes through the membrane includes water and a substantially decreased concentration of organic from the charge liquid. The permeate contains as much as 90 w % or more water, say 98.7 w % water. Permeate is recovered in vapor phase.

Pervaporation may typically be carried out at a flux of 0.5–3, say 1.5 kilograms per square meter per hour (kmh). Typically, the Selectivity may be more than 85 % and typically 85–99 w %, say as high as 99+% water in permeate.

Practice of the process of this invention will be apparent to those skilled in the art from inspection of the following examples wherein, as elsewhere in this specification, all parts are parts by weight unless otherwise stated.

DESCRIPTION OF SPECIFIC EMBODIMENTS

Example I

In this Example, which represents the best mode presently known of carrying out the process of this invention, the carrier layer is a non-woven layer of thermally bonded strands of polyester characterized by a fabric weight of 80±8 grams per square yard, a thickness of 4.2±0.5 mils, a tensile strength (in mechine direction) of 31 psi and (in cross direction) of 10 psi, and a Frazier air permeability of 6 cu.ft/min./sq.ft @0.5 inches of water. The porous support layer is a the commercially available layer of Daicel DUY-L brand of poly acrylonitrile (of molecular weight cut-off of about 40,000) bonded thereto.

The selective separation layer of the membrane is prepared from the Hoechst-Celanese P-600 XE brand of polyethyleneimine polymer resin ($\overline{M}_n$ of 60,000) in 33 w % aqueous solution—Brookfield viscosity @25° C. of 1.04–1.06, and pH of 10–11, having the formula

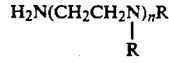

wherein R is H or

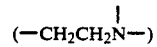

containing 30% primary, 40% secondary, and 30% tertiary amines). This solution is diluted to 1 w % by addition of water.

The assembly of carrier layer and porous support is contacted for 2 minutes with an excess of the diluted aqueous solution (1%) of Corcat P-600 polyethylene imine (PEI). Excess solution is poured off by holding the membrane for 1 minute in a vertical position. Interfacial cross-linking is then effected by adding 1 w % of 2,4-toluene diisocyanate in hexane. Contact at 25° C. is maintained for 30 seconds as interfacial cross-linking is effected. The membrane is then heat cured at 125° C. for 15 minutes.

The membrane assembly so prepared is mounted in a standard pervaporation cell. Charge (and retentate) pressure is atmospheric. Permeate pressure is ca 1 mm.Hg. Permeate is recovered as vapor and condensed against liquid nitrogen.

There is charged to this pervaporation cell a charge solution at 70° C. containing 85 w % isopropanol and 15 w % water. The Selectivity (i.e. w % water in the permeate) is 98.7 w %; and the Flux is 1.49 kmh.

Example II

In this Example, the procedure of Example I is followed except that:

(i) the concentration of the polyethylene imine solution is 0.5 w %; and (ii) the cross-linking agent is hexamethylene diisocyanate in concentration of 0.5 w %.

Selectivity is 89.9 w % Flux is 0.47 kmh.

In Examples III–VI, the charge solution contains 95 w % ethanol and 5 w % water and pervaporation temperature is 80° C.

Example III

In this Example, the procedure of Example I is followed.

Selectivity is 99.4 w %. Flux is 0.72 kmh.

Example IV

In this Example, the procedure of Example II is followed.

Selectivity is 96.4 w %. Flux is 0.56 kmh.

Example V

In this Example, the procedure of Example I is followed except that the time of interfacial cross-linking is 15 seconds rather than 30 seconds as in Example I.

Selectivity is 97.5 w %. Flux is 0.83 kmh.

Example VI

In this Example, the procedure of Example I is followed except that:

(i) the time of interfacial cross-linking is 15 seconds rather than 30 seconds as in Example I; and (ii) the temperature of meat curing is 110° C. rather than 125° C. as in Example I.

Selectivity is 94.1 w %. Flux is 1.03 kmh.

In Examples VII–VIII, the charge solution contains 95 w % acetone and 5 w % water.

Example VII

In this Example, the procedure of Example I is followed.

The Selectivity is 63.1 w %. The Flux is 2.45 kmh.

Example VIII

In this Example, the procedure of Example II is followed.

The Selectivity is 93.3 w %. The Flux is 1.33 kmh.

Example IX

In this Example, the procedure of Example III is followed except in place of acrylonitrile, the porous support layer is Daicel DUS polysulfone.

The Selectivity is 79.9 w %. The Flux is 0.57 kmh.

Results comparable to those of Example I may be attained if the charge solution is:

| Example | Charge Solution |
| --- | --- |
| X | 80 w % ethylene glycol |
|   | 20 w % water |
| XI | 99 w % ethylene glycol |
|   | 1 w % water |
| XII | 92 w % acetic acid |
|   | 8 w % water |
| XIII | 75 w % acetaldehyde |
|   | 25 w % water |

Results comparable to those of Example I may be attained if the cross-linking agent is:

| Example | Cross-linking Agent |
| --- | --- |
| XIV | m-phenylene diisocyanate |
| XV | isophthaloyl dichloride |
| XVI | suberoyl dichloride |

What is claimed:

1. The method which comprises
passing a charge aqueous solution of an organic oxygen-containing liquid component which is soluble in water into contact under pervaportion conditions with, as pervaporation membrane, a non-porous separating polyimine polymer layer which has been interfacially cross-linked with a polyisocyanate or with a poly(carbonyl chloride) cross-linking agent;
maintaining a pressure drop across said membrane thereby forming a high pressure retentate containing increased content of organic oxygen-containing component and decreased content of water and a low pressure permeate of increased content of water and decreased content of organic oxygen-containing component;
maintaining the pressure on the low pressure discharge side of said membrane below the vapor pressure of said permeate thereby maintaining said permeate in vapor phase;
maintaining the pressure on the high pressure retentate side of said membrane above the vapor pressure of said charge aqueous solution and of said retentate and thereby maintaining said charge aqueous solution and said retentate in liquid phase;
recovering said permeate of increased content of water and decreased content of organic oxygen-containing component, in vapor phase from the low pressure discharge side of said membrane; and
recovering said retentate of increased content of organic oxygen-containing component and decreased content of water, in liquid phase from the high pressure side of said membrane.

2. The method of claim 1 wherein said charge organic oxygen-containing component is an alcohol, a glycol, an organic carboxylic acid, a polyol, an aldehyde, or a ketone.

3. The method of claim 1 wherein said charge organic oxygen-containing component is an alcohol.

4. The method of claim 1 wherein said charge organic oxygen-containing component is isopropanol.

5. The method of claim 1 wherein said charge organic oxygen-containing component is ethanol.

6. The method of claim 1 wherein said charge organic oxygen-containing component is a glycol.

7. The method of claim 1 wherein said charge organic oxygen-containing component is ethylene glycol.

8. The method of claim 1 wherein said charge organic oxygen-containing component is an organic carboxylic acid.

9. The method of claim 1 wherein said charge organic oxygen-containing component is a polyol.

10. The method of claim 1 wherein said charge organic oxygen-containing component is an aldehyde.

11. The method of claim 1 wherein said charge organic oxygen-containing component is a ketone.

12. The method of claim 1 wherein said charge organic oxygen-containing component is acetone.

13. The method of claim 1 wherein said cross-linking agent is a diisocyanate.

14. The method of claim 1 wherein said cross-linking agent is toluene diisocyanate.

15. The method of claim 1 wherein said cross-linking agent is phenylene diisocyanate.

16. The method of claim 1 wherein said cross-linking agent is a di(carbonyl chloride).

17. The method of claim 1 wherein said cross-linking agent is suberoyl dichloride.

18. The method of claim 1 wherein said cross-linking agent is isophthaloyl dichloride.

19. The method which comprises
passing a charge aqueous solution containing 95 w % ethanol into contact under pervaporation conditions with, as a pervaporation membrane, a non-porous separating polyethylenimine layer which has been interfacially cross-linked with 2,4-toluene diisocyanate cross-linking agent;
maintaining a pressure drop across said membrane thereby forming a high pressure retentate containing increased content of ethanol and decreased content of water and a low pressure permeate of increased content of water and decreased content of ethanol.
maintaining the pressure on the low pressure discharge side of said membrane below the vapor pressure of said permeate thereby maintaining said permeate in vapor phase;
maintaining the pressure on the high pressure retentate side of said membrane above the vapor pressure of said charge aqueous solution and of said retentate and thereby maintaining said charge aqueous solution and said retentate in liquid phase;
recovering said permeate of increased content of water and decreased content of ethanol in vapor phase, from the low pressure discharge side of said membrane; and
recovering said retentate of increased content of ethanol and decreased content of water, in liquid phase from the high pressure side of said membrane.

20. The method which comprises
passing a charge aqueous solution containing isopropanol into contact under pervaporation conditions with, as a pervaporation membrane, a non-porous separating polyethylenimine layer which has been interfacially cross-linked with 2,4-toluene diisocyanate cross-linking agent;
maintaining a pressure drop across said membrane thereby forming a high pressure retentate containing increased content of isopropanol and decreased content of water and a low pressure permeate of increased content of water and decreased content of isopropanol.
maintaining the pressure on the low pressure discharge side of said membrane below the vapor pressure of said permeate thereby maintaining said permeate in vapor phase;

maintaining the pressure on the high pressure retentate side of said membrane above the vapor pressure of said charge aqueous solution and of said retentate and thereby maintaining said charge aqueous solution and said retentate in liquid phase;

recovering said permeate of increased content of water and decreased content of isopropanol in vapor phase, form the low pressure discharge side of said membrane; and recovering said retentate of increased content of isopropanol and decreased content of water, in liquid phase from the high pressure side of said membrane.

21. The method which comprises passing a charge concentrated aqueous solution of an organic oxygen-containing liquid component which is soluble in water into contact under pervaporation conditions with, as pervaporation membrane, a non-porous separating polyimine polymer layer which has been interfacially cross-linked with a polyisocyanate or with a poly(carbonyl chloride) cross-linking agent;

maintaining a pressure drop across said membrane thereby forming a high pressure retentate containing increased content of organic oxygen-containing component and decreased content of water and a low pressure permeate of increased content of water and decreased content of organic oxygen-containing component;

maintaining the pressure of the low pressure discharge side of said membrane below the vapor pressure of said permeate thereby maintaining said permeate in vapor phase;

maintaining the pressure on the high pressure retentate side of said membrane above the vapor pressure of said charge aqueous solution and of said retentate and thereby maintaining said charge aqueous solution and said retentate in liquid phase;

recovering said permeate of increased content of water and decreased content of organic oxygen-containing component, in vapor phase from the low pressure discharge side of said membrane; and recovering said retentate of increased content of organic oxygen-containing component and decreased content of water, in liquid phase form the high pressure side of said membrane.

22. The method of claim 21 wherein said charge contains at least about 70 wt.% organic oxygen-containing component.

23. The method of claim 21 wherein said charge is an azeotrope of ethanol/water.

24. The method of claim 21 wherein said charge contains at least about 80 w % ethylene glycol.

25. The method of claim 21 wherein said charge contains at least about 85 w % isopropanol.

* * * * *